United States Patent [19]

Sih

[11] Patent Number: 5,128,264
[45] Date of Patent: Jul. 7, 1992

[54] PROCESS FOR PREPARING OPTICALLY ACTIVE 3-HYDROXYBUTANE DERIVATIVES USING LIPASE

[75] Inventor: Charles J. Sih, Madison, Wis.

[73] Assignee: Suntory Limited, Osaka, Japan

[21] Appl. No.: 565,959

[22] Filed: Aug. 13, 1990

[51] Int. Cl.$^5$ .................................. C12P 11/00
[52] U.S. Cl. ........................... 435/280; 435/130
[58] Field of Search ................. 435/280, 130, 198

[56] References Cited

U.S. PATENT DOCUMENTS 4,745,066 5/1988 Hamaguchi et al. ............... 435/280
4,791,059 12/1988 Nakao et al. ........................ 435/198

FOREIGN PATENT DOCUMENTS 369691   5/1990  European Pat. Off.
3245694 10/1988  Japan ................................. 435/130
2-39898  2/1990  Japan .
2-39899  2/1990  Japan .
8910410  1/1989  World Int. Prop. O. .

OTHER PUBLICATIONS

Chinchilla et al., Tetrahedron: Asymmetry 1:575-78 (1990).
Journal of the American Chemical Society, vol. 104, 1982, Washington, D.C. CH.-S. Chen et al. "Quantitative Analyses of Biochemical Kinetic Resolutions of Enantiomers" pp. 7294–7299 *Totality*.

Primary Examiner—Douglas W. Robinson
Assistant Examiner—S. Saucier
Attorney, Agent, or Firm—Oblon, Spivak, McClelland, Maier & Neustadt

[57] ABSTRACT

A process for preparing optically active 1-substituted-3-hydroxybutane or its derivatives of formula (II) or (III)

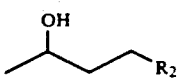

(II)

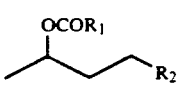

(III)

comprising treating an ester derivative of racemic 1-substituted-3-hydroxybutane of formula (I),

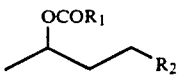 (I)

wherein $R_1$ is chloromethyl group or methyl group and $R_2$ is p-toluenesulfonyloxy group or phenylthio group, provided that when $R_1$ is methyl group $R_2$ is not p-toluenesulfonyloxy group, with a lipase derived from the genus Pseudomonas.

3 Claims, No Drawings

PROCESS FOR PREPARING OPTICALLY ACTIVE 3-HYDROXYBUTANE DERIVATIVES USING LIPASE

BACKGROUND OF THE INVENTION

1. Field of the Invention

The present invention relates to a process for preparing optically active 1-substituted-3-hydroxybutane or its ester derivatives, and, more particularly, to a process for preparing optically active 1-substituted-3-hydroxybutane or its ester derivatives which comprises treating racemic 1-substituted-3-hydroxybutane or its ester derivatives with a lipase.

The products of the present invention can be used, for example as a raw material of azetidinone compounds disclosed in Japanese patent application laid-open No. 207373/1986.

2. Description of the Background Art (3S, 4R)-4-phenylthio-3-[(R)-1-tert-butyldimethyl-sililoxyethyl]-azetidine-2-one and (3S, 4R)-4-acetoxy-3-[(R)-1-tert-butyldimethylsililoxyethyl]- azetidine-2-one are useful compounds as raw materials for the synthesis of penems or carbapenems which are antibiotics. Since these antibiotics are attracting a great deal of attention in recent years and their development are energetically undertaken, the need for the abundant availability of raw materials is increasing.

Although the process of manufacturing (3S, 4R)-4-phenylthio-3-[(R)-1-tert-butyldimethylsililoxyethyl]-azetidine-2-one disclosed in Japanese patent application laid-open No. 207373/1986 may be a useful method, actual practice of the process requires abundant and inexpensive availability of optically active 1,3-butanediol or its derivatives which are the raw materials of the process.

A method of reducing optically active 3-hydroxylbutyric acid derivatives with a hydrogenated metallic reducing agent, a method of reducing 3-oxobutanol with an asymmetric reducing agent, a method of fractionating 1,3-butandiol derivatives with a fractionator, and the like are known as processes for manufacturing optically active 1,3-butanediol. All these methods, however, have problems in the costs of reducing agents or fractionating agents, processability of the reactions, yields, optical purity of the products, and the like, when they are applied to a large scale production. Since none of the processes are practically useful, development of a new process is desired.

In view of this situation, the present inventors have undertaken extensive studies, and have found that an optically active 1-substituted-3-hydroxybutane or its derivative represented by formula (II) or (III),

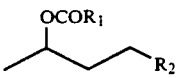

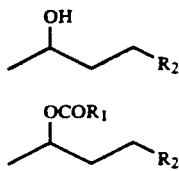

could be prepared in a high yield and in high optical purity by a simple process in which an ester derivative of racemic 1-substituted-3-hydroxybutane of formula (I),

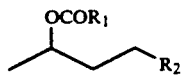

is treated with a lipase to effect asymmetric hydrolysis.

In the above formulae (I) to (III), $R_1$ is an alkyl group having 1-8 carbon atoms, an aryl group having 6-10 carbon atoms, an alkoxy group having 1-6 carbon atoms, or an aryloxy group having 6-10 carbon atoms, wherein hydrogen atoms on the carbon atoms of the alkyl, aryl, or alkoxy group may optionally be substituted by alkyl, aryl, hydroxyl, alkoxy, alkylthio, or arylthio group, and $R_2$ is a halogen atom, an alkylsulfonyloxy group having 1-8 carbon atoms, an arylsulfonyloxy group having 6-10 carbon atoms, an alkylthio group having 1-8 carbon atoms, or an arylthio group having 6-10 carbon atoms, wherein hydrogen atoms on the carbon atoms of the alkylsulfonyloxy, arylsulfonyloxy, alkylthio, or the arylthio group may optionally be substituted by halogen, alkyl, aryl, hydroxyl, or alkoxy group, and in formulae (II) and (III) the secondary hydroxyl group has either R or S configuration.

SUMMARY OF THE INVENTION

Accordingly, an object of the present invention is to provide a process for preparing an optically active 1-substituted-3-hydroxybutane or its derivative represented by formula (II) or (III),

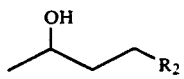

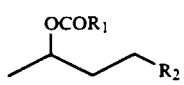

wherein $R_1$ is an alkyl group having 1-8 carbon atoms, an aryl group having 6-10 carbon atoms, an alkoxy group having 1-6 carbon atoms, or an aryloxy group having 6-10 carbon atoms, wherein hydrogen atoms on the carbon atoms of the alkyl, aryl, or alkoxy group may optionally be substituted by alkyl, aryl, hydroxyl, alkoxy, alkylthio, or arylthio group, and $R_2$ is a halogen atom, an alkylsulfonyloxy group having 1-8 carbon atoms, an arylsulfonyloxy group having 6-10 carbon atoms, an alkylthio group having 1-8 carbon atoms, or an arylthio group having 6-10 carbon atoms, wherein hydrogen atoms on the carbon atoms of the alkylsulfonyloxy, arylsulfonyloxy, alkylthio, or the arylthio group may optionally be substituted by halogen, alkyl, aryl, hydroxyl, or alkoxy group, and the secondary hydroxyl group has either R or S configuration, which comprises treating an ester derivative of racemic 1-substituted-3-hydroxybutane of formula (I), wherein $R_1$ and $R_2$ have the same meanings as defined above, with a lipase.

In a preferred embodiment of the present invention, the compound of formula (I) is an ester derivative of 1-p-toluenesulfonyloxy-3-hydroxybutane.

In another preferred embodiment of the present invention, the compound of formula (I) is an ester derivative of 1-phenylthio-3-hydroxybutane.

Other objects, features, and advantages of this invention will appear more fully from the following description.

DETAILED DESCRIPTION OF THE INVENTION AND PREFERRED EMBODIMENTS

There are a number of reports about the assymetric hydrolysis of racemic compounds using lipase. Few of them, however, have confirmed their efficiency quantitatively, nor few processes have been developed to a commercially competent stage. The present inventors have conducted studies about quantitative analysis of enzymatic or biological resolution products, and contributed a report dealing with the relationship between the degree of conversion (c), optical purity or enantiometric excess (ee) of the product, enantiometric ratio (E value) [J. Amer. Chem. Soc. 104, 7294 (1982)]. The effect of the present invention have specifically been proven by the calculation of the E value according to the following equation.

$$E = ln[1-c(1+ee(P)]/ln[1-c(1+ee(P)]$$

wherein,
E (E value): enantiometric ratio
c (%): degree of conversion
ee(P): enantiometric excess (ee) of the product An ester derivative of racemic secondary alcohol represented by formula (I) can be prepared by a conventional esterification process. A typical example is a condensation reaction of an alcohol represented by formula (IV),

(IV)

wherein $R_2$ has the same meaning as defined above, and a carboxylic acid of the formula $R_1COOH$ (V), wherein $R_1$ has the same meaning as defined above, in the presence of an organic acid such as p-toluenesulfonic acid or the like or a mineral acid such as hydrochloric acid, sulfuric acid, or the like. Alternatively, instead of a carboxylic acid, a carboxylic acid halide, a carboxylic ester, or carboxylic acid anhydride of formula (VI),

$R_1COY$ (VI)

wherein $R_1$ has the same meaning as defined above and Y is a halogen atom, an alkoxy group, or an acyloxy group, can be used for the condensation reaction with the alcohol of formula (IV) in the presence of an organic base such as triethylamine or the like or an inorganic base such as sodium hydroxide.

There are no specific restrictions as to the carboxylic acids, acid halides, esters, or acid anhydrides represented by formula (V) or (VI). Preferable compounds are linear alkyl carboxylic acids, e.g. acetic acid, propionic acid; branched alkyl carboxylic acids, e.g. isobutyric acid, pivalic acid; aryl carboxylic acid, e.g. benzoic acid; aralkyl phenyl; aralkyl carboxylic acid, e.g. phenylacetic acid; and acid halides, esters, or acid anhydrides derived from these carboxylic acids. The type of carboxylic acid is determined by the type of lipase used.

The reaction of a compound of formula (I) with a lipase is usually carried out in a buffer solution at temperature, preferably, of 20°-50° C. Although there are no specific restrictions as to the pH of the buffer solution, an optimum pH is selected depending on the type of lipase used. Lipases derived from microorganisms are preferable, with particularly preferable lipases being those derived from the genus Pseudomonas. There are no specific restrictions as to the purity of the lipase used. For example, cultured living cells or deceased cells, either purified or unpurified, can be used.

The amount of lipase used is selected from the range of 0.0001 to 100% by weight, and the concentration of the reaction substrate is selected from the range of 10 to 200% (W/V). The reaction time is about 5 to 100 hours, although it is variable depending on the type of lipase and the type of substrate used.

After completion of the reaction, the reaction mixture is extracted with a solvent which is not miscible with water, and the extract is dried and concentrated to give a mixture of the target optically active alcohol and an ester derivative which is the enantiomer of the alcohol. The alcohol and the ester are separated from each other and purified by means of silica gel column chromatography, distillation, or the like.

Alternatively, the reaction mixture is left to stand to separate the oil layer and the water layer, following which the oil layer is washed several times with water or a water soluble solvent to obtain an almost pure ester as the residual oil.

An alcohol, e.g. methanol, ethanol; a ketone, e.g. acetone, methyl vinyl ketone; an ether, e.g. tetrahydrofuran; a nitrile, e.g. acetonitrile; or the like can be used as a water soluble solvent.

The mother liquor obtained in the above procedure can be collected and concentrated to give oil components contained therein. When the ester is contained in the oil components, an additional amount of the ester compound is produced by repeating the above procedure. In this way, the target alcohol compound can be obtained ultimately in an almost pure form. Since this fractional extraction method can produce the target alcohol compound or ester without procedures such as chromatography, distillation, or the like, it can be applied more advantageously to large scale production of unstable compounds or compounds for which a high degree of purification is not required.

Other features of the invention will become apparent in the course of the following description of the exemplary embodiments which are given for illustration of the invention and are not intended to be limiting thereof.

EXAMPLES

Example 1

Into a suspension of 200 mg of (±)-3-acetoxy-1-p-toluenesulfonyloxybutane in 2 ml of 0.2M phosphate buffer (pH 8), 100 mg of lipase shown in Table 1 below was added, and the mixture was stirred at 24° C. until a degree of conversion of about 50% was achieved, upon which ethyl acetate was added to separate the water layer and the organic layer. The organic layer was dried over anhydrous sodium sulfate, and concentrated under a reduced pressure. The residue was purified over silica gel column chromatography to produce a pure ester compound and alcohol compound. The enantiometric excess purity (ee%) of the ester compound was determined by the measurement of 200M Hz PMR in the presence of Eu(hfc)₃. The results are given in Table 1.

TABLE 1

| Lipase | Reaction time (hr) | Ester compound Absolute configuration | ee % | Alcohol compound Absolute configuration | ee % | c Value (%) | E Value |
|---|---|---|---|---|---|---|---|
| K-10 | 44 | S | 99 | R | 97 | 49 | >100 |
| AK | 72 | S | 71 | R | 83 | 46 | 23 |
| P-30 | 17 | S | 85 | R | 95 | 47 | >100 |

Example 2

An ester compound and an alcohol compound were prepared in the same manner as in Example 1, except for using 200 mg of (±)-3-chloroacetoxy-1-p-toluenesulfonyloxybutane and 40 mg of lipase. The results are given in Table 2.

TABLE 2

| Lipase | Reaction time (hr) | pH of 0.2M Phosphate buffer | Ester compound Absolute configuration | ee % | Alcohol compound Absolute configuration | ee % | c Value (%) | E Value |
|---|---|---|---|---|---|---|---|---|
| K-10 | 13.5 | 8.0 | S | 94 | R | 97 | 53 | 65 |
| AK | 13.5 | 8.0 | S | 71 | R | 83 | 53.5 | 23 |
| P-30 | 7 | 7.0 | S | 90 | R | 95 | 48 | >100 |

Example 3

Into a mixture of 3 g of 9.4 mM (±)-3-chloroacetoxy-1-p-toluenesulfonyloxybutane in 2 ml of 1 M phosphate buffer (pH 8.0), 10 mg of lipase P-30 was added, and the mixture was vigorously stirred at 23° C. for 57 hours. The resultant reaction mixture was transferred into a separating funnel and allowed to stand to separate a lower layer of viscous oil. 200 mg of the oil was subjected to silica gel column chromatography to separate 60 mg of (R)-3-hydroxy-1-p-toluenesulfonyloxybutane; ([α]=−20° (c=1.5, EtOH),ee=98%), and 95 mg of (S)-3-chloroacetoxy-1-p-toluenesulfonyloxybutane; ([α]=+17.0°(c=2.62,EtOH),ee=69%).aaa The residual viscous oil was extracted three times with 20 ml of a water-methanol mixture (v/v, 1:1) to obtain 890 mg (29.5%) of a pure ester compound as a residue. The water-methanol layers were collected and methanol was removed therefrom by concentration under a reduced pressure to obtain an oil component. 18 ml of a water-methanol mixture (v/v, 1:0.9) was added to the oil, the mixture was vigorously stirred, and allowed to stand to separate an oil layer, from which methanol was removed by concentration. To the water layer was added 15-18 ml of methanol to make the water:methanol to 1:0.9 (v/v). This procedure was repeated three times to obtain 700 mg (31%) of an alcohol compound as a residue. In addition to the alcohol compound, 700 mg of an ester-alcohol mixture was recovered.

Example 4

Ester compounds and alcohol compounds were prepared in the same manner as in Example 1, except for using 100 mg of (±)-3-acetoxy-1-phenylthiobutane and 25 mg of a lipase shown in table 3. The results are given in Table 3.

TABLE 3

| Lipase | Reaction time (hr) | Ester compound Absolute configuration | ee % | Alcohol compound Absolute configuration | ee % | c Value (%) | E Value |
|---|---|---|---|---|---|---|---|
| K-10 | 13.5 | S | 94 | R | 97 | 28 | 20 |
| AK | 13.5 | S | 71 | R | 83 | 37 | 10 |
| P-30 | 7 | S | 85 | R | 95 | 36 | 17 |

Obviously, numerous modifications and variations of the present invention are possible in light of the above teachings. It is therefore to be understood that within the scope of the appended claims, the invention may be practiced otherwise than as specifically described herein.

What is claimed is:

1. A process for preparing an optically active 1-substituted-3-substituted butane represented by either formula (II) having an R configuration or (III) having an S configuration

 (II)

 (III)

wherein R₁ is chloromethyl group or methyl group and R₂ is p-toluenesulfonyloxy group or phenylthio group, provided that when R₁ is methyl group, R₂ is not p-toluenesulfonyloxy group which comprises treating an ester derivative of racemic 1-substituted-3-hydroxybutane of formula (I)

 (I)

wherein R₁ and R₂ have the same meanings as defined above, with a lipase derived from the genus Pseudomonas.

2. A process according to claim 1, wherein said compound of formula (I) is an ester derivative of 1-p-toluenesulfonyloxy-3-hydroxybutane.

3. A process according to claim 1, wherein said compound of formula (I) is an ester derivative of 1-phenylthio-3hydroxybutane.

* * * * *